United States Patent [19]

Ernst

[11] Patent Number: 5,309,754

[45] Date of Patent: May 10, 1994

[54] HARDNESS TESTER AND METHOD FOR MEASURING THE HARDNESS OF METALLIC MATERIALS

[76] Inventor: Alfred Ernst, Via Ronchetto, 3, CH-6814 Cadenpino, Switzerland

[21] Appl. No.: 859,726

[22] PCT Filed: Oct. 16, 1991

[86] PCT No.: PCT/EP91/01965

§ 371 Date: Jun. 12, 1992

§ 102(e) Date: Jun. 12, 1992

[87] PCT Pub. No.: WO92/08119

PCT Pub. Date: May 14, 1992

[30] Foreign Application Priority Data

Oct. 24, 1990 [IT] Italy .................. 83639 A/90

[51] Int. Cl.$^5$ .................................................. G01N 3/48
[52] U.S. Cl. ............................................................. 73/81
[58] Field of Search ................................ 73/81, 28, 83

[56] References Cited

U.S. PATENT DOCUMENTS

| | | | |
|---|---|---|---|
| 1,781,002 | 11/1930 | Esnault-Pelterie | 73/81 |
| 2,122,203 | 6/1938 | Gogon | 73/83 |
| 3,416,367 | 12/1968 | Ernst | 73/83 |
| 4,445,367 | 5/1984 | Goldsmid | 73/81 |
| 4,667,509 | 5/1987 | Tobolski et al. | 73/83 |
| 4,984,453 | 1/1991 | Enomoto | 73/81 |

FOREIGN PATENT DOCUMENTS

| | | | |
|---|---|---|---|
| 1060211 | 3/1954 | France | 73/81 |
| 86/06833 | 11/1986 | World Int. Prop. O. | 73/81 |
| 88/03644 | 5/1988 | World Int. Prop. O. | 73/81 |

OTHER PUBLICATIONS

Howes, V. R. et al, Hardness Measurement At Constant Depth Using An Indenter Partially Coated With A Conducting Film, Journal of Physics E/Scientific Instruments 20 (1987) Dec., No. 12 Bristol, Gr. Britain, pp. 1507–1510.

Notification of Transmittal and International Search Report PCT/EP91/01965, May 2, 1992.

Primary Examiner—Hezron E. Williams
Assistant Examiner—Daniel S. Larkin
Attorney, Agent, or Firm—Pollock, Vande Sande & Priddy

[57] ABSTRACT

The hardness of a metal sample is determined using a hardness tester provided with an indenter having an indenting tip and means for loading the indenter. The method comprises employing an electrically conductive indenting tip and connecting the indenter and the metal sample to the input terminals of an electric resistance measuring apparatus. The indenter is loaded up to a preset load on a reference metal sample having a known hardness and detecting the contact resistance under the load. The tester is functionally set on a metal sample to be tested and gradually the indenter is loaded until the same electrical contact resistance as detected on the reference sample is measured by the electrical resistance measuring apparatus and the load which is actually applied to the indenter is read. The hardness of the tested sample is determined through a proportionality relationship between the preset load applied to the reference sample and the load applied to the tested sample.

4 Claims, 2 Drawing Sheets

HARDNESS TESTER AND METHOD FOR MEASURING THE HARDNESS OF METALLIC MATERIALS

TECHNICAL FIELD

The present invention relates to a hardness tester for metals and metal alloys capable of expressing comparative hardness values in Vikers or Brinnel scales, and providing for a direct reading without the need for carrying out microscopic indentation size measurement or detecting indenter's displacement.

BACKGROUND ART

Hardness testers are instruments which are well known to the skilled technician. The apparatus, which may take different forms, comprises an indenter constituted essentially by a stylus assembly which may assume various forms depending on the type of sample to be tested provided with an indenting tip of a hard and undeformable material, commonly a diamond or a hard metal, and a loading system for applying a certain load. The hardness assessment is generally a multistep test whereby the size of the indentation produced by the indenting tip on the surface of the piece to be tested under a certain load applied to the indenter, or the depth of penetration of the indenter is measured.

The tip of the indenter may have a conical, a spherical (Brinnel) or square piramidal (Vikers) form. The diamond or the hard metal are the materials commonly used for making these tips which must be sufficiently hard so as not to be scratched by the material being tested and undeformable under the test load.

A bench-type apparatus comprises usually a support structure, a loading system through which it is possible to load and by an inventory of implements for permitting to select a certain configuration of the indenter, suitable for the piece to be tested. e.g. for effecting tests on external or internal surfaces of a machined piece of machinery.

Where the indentation cannot be viewed through an optical microscope, for example in the case of an internal surface of a tubular piece, the assessment of the hardness must necessarily be based upon a micrometric determination of the depth of penetration of the indenter tip in the material being tested, according to the capabilities of the known apparatuses. These measurements of size and/or depth of an indentation are burdensome and are often a source of evaluation errors.

In U.S. Pat. No. 4,848,141 and in the Article "Measurements of Hardness at Indentation Depths as Low as 20 Nanometers"; by W. C. Oliver, R. Hutchings and J. B. Pethica, pp 90-108, ASTM Special Technical Publication No. 889, 1986, a method of determining hardness, yield strength, and other mechanical parameters of a material are disclosed wherein the load applied to a microindenter and the displacement of the indenter after the establishment of contact with the surface of the sample are electronically measured and elaborated to obtain the value of the particular mechanical parameter.

On the other hand, the contact area between two bodies is difficult to determine when the area of contact is less than a few square microns. There have been prior attempts to obtain such a measurement by determining the electrical resistance at the junction. However, to date, such a technique has never found application in indenter-type hardness testing apparatus which for other reasons must utilize an intrinsically insulating indenter tip, such as a diamond tip.

SUMMARY OF THE INVENTION

There is a necessity of an apparatus for measuring the hardness of surfaces different to access to, such as the side of the tooth of a gear or internal surfaces which cannot be examined under a microscope and easy to be used and which positively reduces the probability of a reading error by the operator.

This objective is attained by means of the apparatus objects of the present invention, which is advantageously capable of providing a precise indication of the hardness of a sample in an easy manner while reducing the probability of an error of assessment by the operator.

Basically the hardness tester of the present invention utilizes an instrumental determination of an electrical contact resistance for determining the hardness of a metallic sample. The contact resistance which is measured is the electrical contact resistance between the tip of the indenter and the metallic sample being tested. This resistance is a function of the contact surface area, which is in turn a function of the indentation produced by the tip in the metallic sample being tested, under the applied load. To this end, the indenter's tip as well as the metallic sample being tested, are connected to a resistance-test circuit and the indenter's tip is made with a substantially conductive material having an electrical conductivity which is relatively low and preferably lower or equal to about a tenth of the electrical conductivity of the metallic sample being tested. This fact greatly increases the sensibility of the measurement system. In other words, a "concentration" of the resistance for the whole electric path of the resistance measuring at the indenter's tip, establishing the contact with the metallic sample circuit which inevitably includes a metallic tip holder and a metallic sample support beside the electrical wire connections to the input terminals of the resistance measuring instruments or resistance measuring circuit, determines a greater usable gradient of variation of measured resistance $\Delta R$ in function of a given increment of the penetration of the indenting tip in the metallic sample being tested.

The actual value of the hardness of the sample is preferably expressed by the hardness tester through a comparison with a similar electrical contact resistance determination performed on the surface of a "master sample" of precisely known hardness. This comparison may be effected by determining the difference between the loads which attain the same contact resistance on the master sample and on the successively tested sample. In this way, by exactly knowing the hardness of the "master sample", the hardness of the test sample may be readily read from a standard Brinnel or a standard Vikers scale by utilizing the difference between the loads attaining the same contact resistance, i.e. the same area of contact, i.e. the same size of indentation, to read the correct hardness value of the test sample.

The master sample of known hardness which is used for a particular hardness assessment should preferably be a master having a hardness value which is relatively close to the expected hardness of the test sample and a reasonable inventory of master samples of different precisely known hardness will readily permit to accomplish such a preferable condition of comparison.

The comparison method of measurement though implying a two step test procedure practically elimintates all problems which would be associated otherwise to the periodical trimming of the apparatus response. In practice, the comparison method has been found to be effective in balancing out the effects of innumerable causes of variance of the electrical contact resistance which is subject to the influence of the different conditions under which the measurement is carried out. In this connection, as it will be further described later in the description, carrying out the test with the surface of both the test sample as well as of the master sample wetted with oil has been found to further improve the repeatability of the contact resistance measurements and consequent hardness assessments.

The different aspects and advantages of the invention will be more easily appreciated through the following description of several embodiments of the invention and by reference to the attached drawings.

BEST AND VARIOUS MODES FOR CARRYING OUT INVENTION

For ease of description, the same parts or parts of the measuring apparatuses shown which are functionally equivalent among each other are indicated with the same reference number in the figures.

Figure 1:
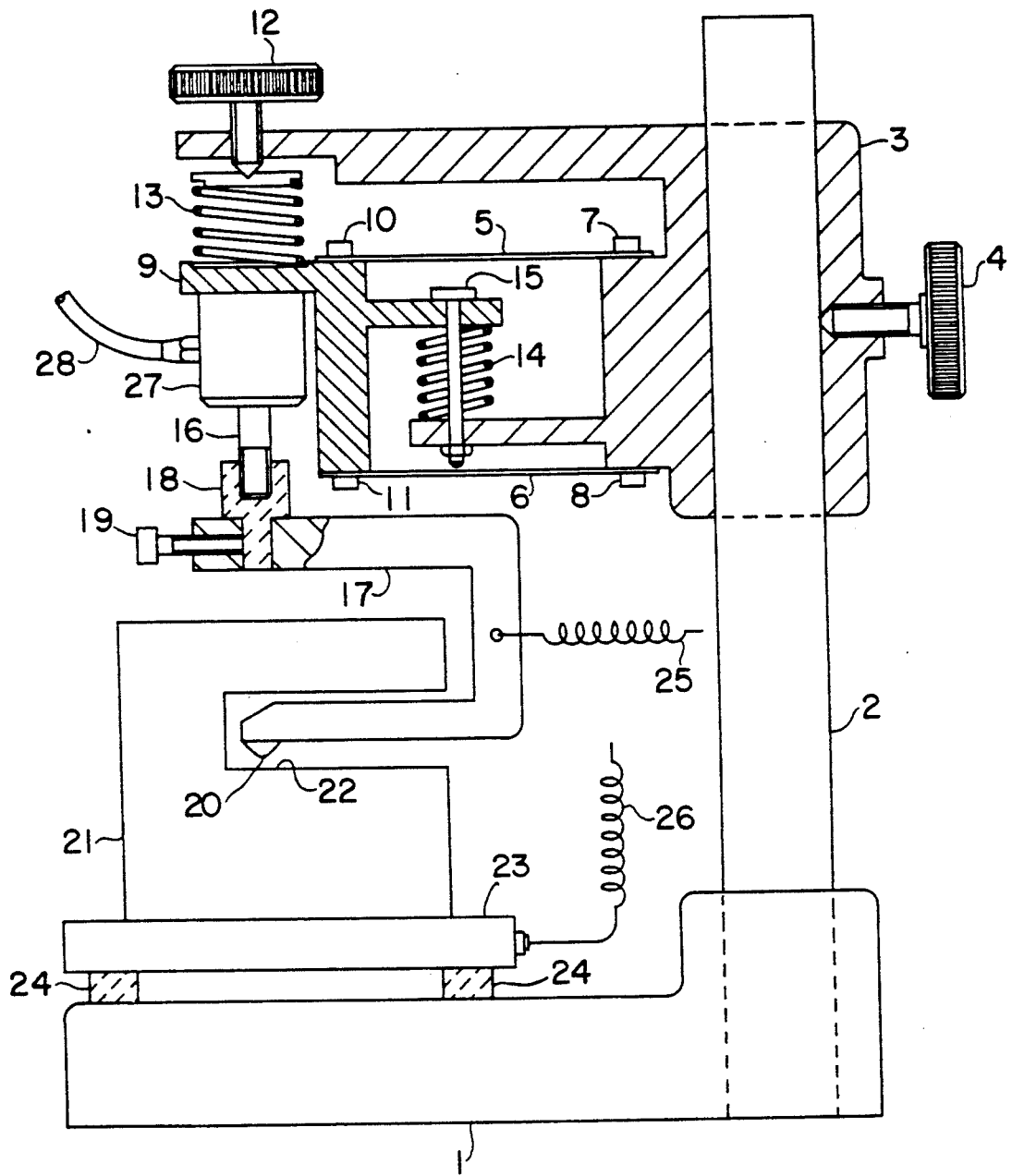
FIG. 1 is a schematic sectional elevation view of a bench-type hardness tester according to the present invention.

With reference to FIG. 1, the hardness tester depicted therein comprises a support base 1, a stanchion structure 2 on which a shelf body 3 may be slidibly set and blocked in a fixed position by means of a blocking knob 4. A mobile loading body 9 is assembled on the shelf body 3, and is suspended therefrom by means of two steel leaf-springs 5 and 6 which are fixed at one end to the shelf body 3 by means of the screws 7 and 8. The loading body 9 is fixed to the other end of the two suspending leaf-springs 5 and 6 by means of the screws 10 and 11. The mobile body 9 may be loaded downward by means of the loading screw 12 acting on the mobile body 9 through a compression spring 13 which exerts a force on the mobile body 9 in opposition to the force exerted on the same body 9 by the restraining or suspension spring 14, the pre-compression of which may be adjusted by means of the stopper 15.

By interposing a boss 18 of an electrical insulating material, for example of an insulating ceramic, a "U" shaped indenter holder 17, suited for interior surfaces, is attached to the lower end of the load pin 16 which is fixedly connected to the mobile body 9 by means of the set screw 19.

The indenter's tip 20 is mounted into a recess at the end of the indeter body 17. The metallic sample to be tested is identified with 21 and the determination of the harness may be carried out on the internal surface 22 of the piece.

The metallic sample 21 rests on a metal support 23 (anvil) which is electrically isolated from the base 1 by placing therebetween electrically insulating supports 24, e.g. of a nonconductic ceramic material.

Wire connection 25 and 26 to a resistance measuring apparatus are depicted.

The load which is applicable by means of the handwheel 12 may be detected by means of strain gages mounted on the block 27 and the terminals of the strain gages are connected though the cable 28 to a suitable measuring instrument, provided with an analog or digital display (not visible in FIG. 1) of the load which is applied to indenter.

Figure 2:
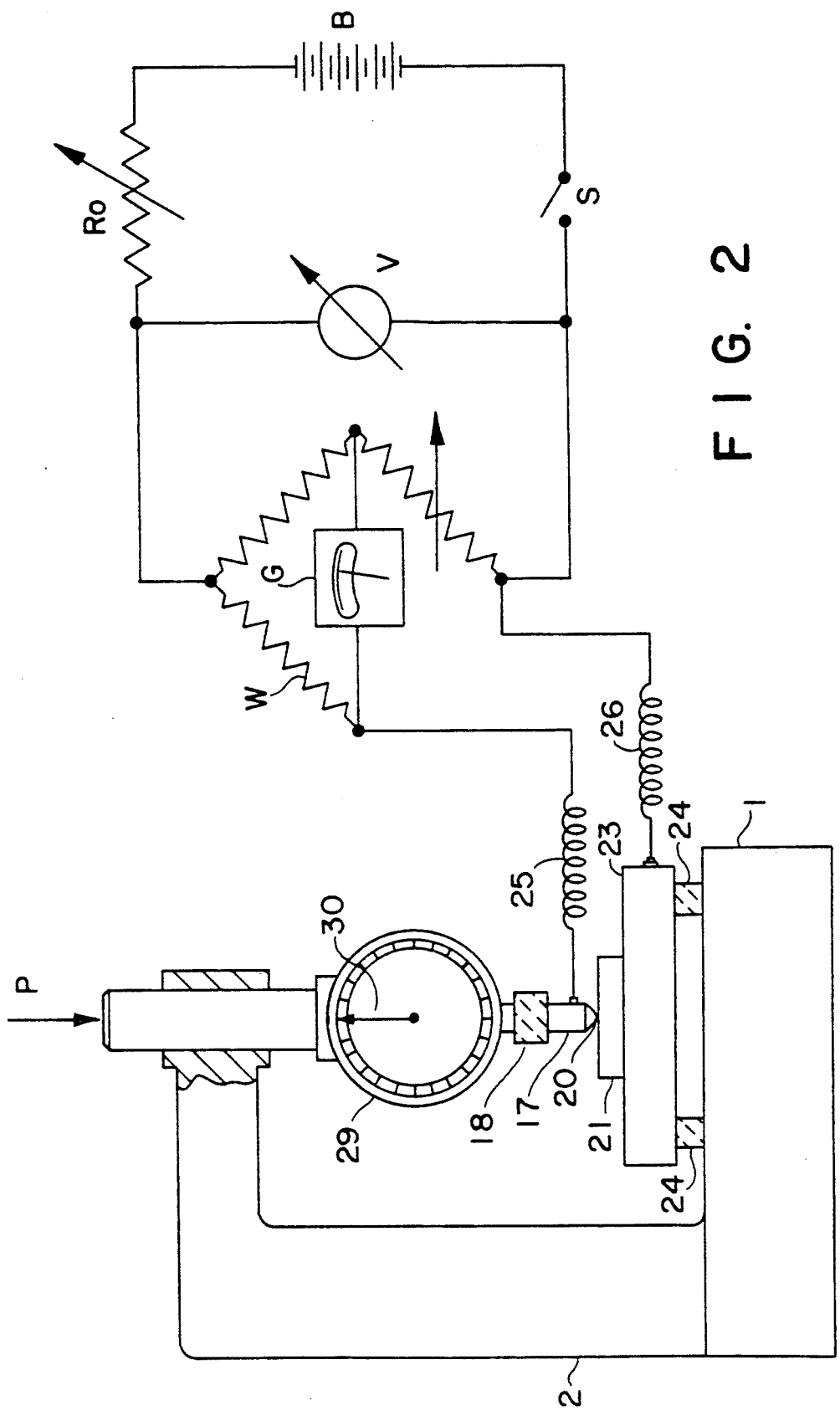
FIG. 2 is a schematic view of a hardness tester of the present invention schematically showing a resistance testing circuit.

FIG. 2 depicts schematically a basic system for determining the hardness by means of the apparatus of the invention.

In FIG. 2 the hardness tester is schematically depicted by utilizing the same number for identifying the components analog to those already described in connection with FIG. 1. In this schematic showing of FIG. 2, the load P which is applied to the indenter is displayed on the scale 29 where an index 30 indicates the value of the load which is applied to the indenter 17, i.e. to the indentation tip 20, by acting on the loading handwheel (12 in FIG. 1).

As shown, the electrical wire connections 25 and 26 for the "electrical series" formed by the conducting metal body 17 of the indenter, the indentation tip 20, the test sample 21 and the anvil 23 and which "series" of electrically conducting elements is isolated by the insulators 24 and 18, are shown coupled to a Wheatstone test-bridge, indicated with W as a whole, which is powered by the battery B through the rheostat RO and the switch S, at a voltage which is measured by the voltmeter V, while the equilibrium condition of the test-bridge is determined by means of the galvanometer G.

The illustration of the electrical contact resistance measuring apparatus in the form of a classical Wheatstone bridge test circuit, has a clear illustrative and nonlimitative purpose, being the Wheatstone bridge the classical test circuit for resistance measurements. Of course any other instrument capable of measuring electrical resistance with sufficient degree of precision can obviousuly be utilized in the hardness tester of the invention, whether or not such an instrument incorporates a Wheatstone-bridge test circuit.

According to the preferred method of assessing hardness of a test sample by means of the apparatus of the invention, a reference or blank or master sample having a precisely known hardness, sufficiently close in order of magnitude to the presumed hardness of the surface of the sample to be tested, is placed on the anvil 23. The hardness of the master sample which is exactly known may be conventionally expressed in terms of specific load in a Vikers and/or Brinnel scale, whereby the hardness value corresponds to the load expressed in kilograms per square millimeter of indentation area produced on the surface of the material. A certain reference load is applied to the indenter by reading it on the scale of the dynamometer 29 and such a reference load may be chosen in function of the type of surface treatment to which the sample to be tested has been subjected, i.e. to the order of magnitude of the presumed hardness of the sample to be tested. This produces a certain indentation on the surface of the master or reference sample.

Under this loading condition, the Wheatstone bridge is balanced by acting on the variable resistance of the bridge, according to well known resistance measuring procedures, or the resistance is accurately determined by any other means.

The load is released and the reference sample is substituted with the sample to be tested on the anvil 23 of the instrument.

The dynamometer is progressively and gradually loaded until the Wheatstone bridge reaches again a balance condition.

When the bridge is returned to the balance condition the load corresponding to such a renewed balance condition of the contact resistance measuring bridge is read off the scale 29 of the dynamometer.

In this way, it is established that the resistance of the electrical series is equal to the resistance attained when testing the reference sample and because the electrical resistance of the relative branch of the Wheatstone bridge between the wire connection 25 and 26 is substantially represented by the contact resistance between the indenter's tip 20 in function of the contact area of the latter with the sample being tested, the equality of resistance is indicative of an equality of indentation, i.e. of contact area between the indenting tip 20 and the metallic sample being tested. At this point the load which is read off the scale 29 of the dynamometer is in the same ratio with the load which was applied on the reference sample for establishing such a contact resistance as the respective hardnesses. For example, if on the reference sample was applied a load of 5 kilograms and on the subsequently tested sample the load for balancing the contact resistance bridge circuit is of 4,5 kilograms, the hardness of the sample being tested may be correctly assessed as being 10% lower than the known hardness of the reference sample.

Such a comparison condition for relatively assessing the hardness will be as precise as less significant is the electrical resistance contribution of the metallic masses of the parts 17, 21 and 23, electrically connected in series of FIG. 2, as well as of the wire connections 25 and 26, in respect to the electrical contact resistance between the indenter's tip 20 and the metal sample. An electrical conductivity of the material with which the indenter's tip 20 is made, lower than about 10 times the electrical conductivity of the material of the piece to be tested 21 or more generally of the electrical conductivity of metals and metallic alloys in general, permits to attain a remarkable precision in the hardness assessment according to the comparative method described above.

Such an upper limit of electrical conductivity of the indenter's tip, permits a sufficient sensitivity of the measuring system and allows to satisfactorily use it also for determining the hardness of samples made of particularly resistive metal alloys or other materials which are intrinsically very resistive such as titanium, tungsten, "cermets" and the like. Of course, when the instrument must be used for assessing the hardness on highly conductive metallic materials such as steel, copper, aluminum, etc., the indenter's tip may have a much greater electrical conductivity in absolute terms.

The lower limit of an electrical conductivity of the material with which the indenter's tip is made, will be such as to permit the measurement of an electrical resistance which in absolute terms is not eccessively high, which fact would otherwise represent a factor of reduced precision of the resistance measurements because of intrinsic sensitivity limitations of the electrical resistance measuring instrument.

Materials which may be used for manufacturing a suitably conductive indenter's tip of the hardness tester may be of various kind although possessing sufficient hardness and undeformability properties under load and an electrical conductivity fitting the above-mentioned limits. Borides, carbides, nitrides, hydrides, oxyborides, oxynitrides, oxycarbides, perowskites, delofossites, spinels and mixtures of the same materials may suitably form the indenter's tip of the invention. These materials may be shaped by sintering and diamond ground for producing the desired profile of the tip. Most preferably the tip is a crystal having sufficient electrical conductivity, such as for example a type IIb diamond crystal. More preferably the electrical conductivity of an indenter's diamond tip is raised by means of an ion implantation treatment. It has been found that an ion implantation of diamond with nitrogen at a level of $10^{16}$ ions per centimeter square, produces an adequately conducting "skin" of the tip. The implantation is normally carried out on the diamond tip after it has been already set in the indenter's body and ground to the desired shape, by exposing the indenter assembly to the flux of accelerated nitrogen ions inside an ion implantation vessel. Of course ions other than nitrogen may be satisfactorily implanted in a diamond crystal for imparting a sufficient electrical conductivity to at least a superficial "skin" layer of the tip.

When employing an implanted crystal tip set in a metallic indenter body, the electrical continuity between the tip and the metallic indeter's body in which the tip is set, may be ensured by depositing a conducting metal coating, for example by a chemical vapor deposition (CVD) process, after having masked the vertex of the indenting implanted crystal tip. The conductive coating deposited on the unmasked portion of the implanted crystal tip and on the adjacent surface of the metallic indenter body in which the tip is solidly set, provides a conductive "bridge" between the relatively conductive implanted "skin" portion of the crystal tip and the metallic indenter body. This, beside preventing a criticity of electrical continuity between the crystal tip and the metallic indenter body, further "concentrates the resistance signal" in the contact area established by the indenter's tip with the metallic test sample. Of course the metallic coating on the surface of the indenter's tip is arrested (by the masking) at a sufficient distance from the vertex of the indenter's tip so as not to come in contact with the metallic sample.

According to a preferred method of the invention, the repeated electrical resistance measurements (on the reference and on the test samples) are performed after having wetted the surface of the metal sample with oil, such as a lubricating oil. To this effect the samples may also be completely immersed in a pool of oil while measuring the comparative contact resistances. It has been found surprisingly that by conducting the measurements in oil, the repeatability of the contact resistance measurements under identical load conditions, is enhanced. This may be explained by assuming that the oil dissolves eventual residual traces of grease which would otherwise remain undisplaced under the relatively high specific loads at the indenter's tip-sample interface; or by a cleansing action of the oil on microscopic metallic particles whose presence could affect the contact resistance and which may be detached and electrically neutralized (isolated) by the oil; or the action of the oil may be that of increasing the "definition" of the contact areas in presence of the plastic flow of the indented metal. An alternative procedure to the wetting the surface with oil prior to indent the surface and measure the electrical resistance is to accurately clean the surface of the sample to be indented. However this latter technique has been found inferior to conducting the test in presence of oil, in terms of repeatability of the electrical resistance measurements.

Naturally the hardness tester of the invention may be realized in different forms adapted to specific uses. The apparatus may be constructed in the form of a bench-type tester or it may be made in a form of a portable instrument for field use. In this latter form the instrument may be readily reduced in size and have a simplified configuration wherein the load can be manually applied by a simple pushing-action. It has in fact been found that the measuring system well tolerates slight oscillations of the tip's axis of application of the load which may occur during the electrical resistance measurements. This may be explained by the fact that the electrical contact surface between the indenter's tip and the sample depends basically from the specific load (i.e. from the hardness of the sample). For this reason even for small variations of the angle of incidence of the axis of the indeter's tip and the surface being indented, the variations of the contact resistance are negligeable.

Naturally the hardness tester of the invention may be easily automatized by providing for a motorized gradual load application which may be easily controlled. For example when repeating the contact resistance test on a first sample, the load application may be automatically arrested upon attainment of equilibrium of the resistance measuring bridge circuit. The automation may also provide for calculation and display of the actual hardness of the tested material. Moreover the system may be equipped with a programmable data-recording and processing unit for a complete analysis of the hardness determination.

The electrical contact resistance measurements which are used for comparing and determining hardnesses, instead of being end-point type determinations, may be carried out in the form multiple point determinations under progressively increased loads both on the reference sample of known hardness and subsequently on the sample to be tested. The various pair of comparable contact resistance measurements may be analysed for providing information on the variation of hardness in function of the depth of penetration of the indeter in the sample being tested. Also in a case such as the above, the provision of automatic data-collecting and data-processing units will greatly simplify and make a thorough analysis of the properties of the tested sample practically immediate.

I claim:

1. A method for determining the hardness of a metal sample by using a hardness tester provided with an indenter having an indenting tip of a hard and undeformable material and means for loading said indenter with a certain load for producing the penetration of said tip in the metallic sample, the depth of penetration and/or the width of the indentation produced under a given load providing a measure of the hardness of the material, characterized by comprising:
   utilizing an electrically conductive indenting tip and connecting said indenter and said metallic sample to the input terminals of an electric resistance measuring apparatus;
   loading said indenter up to a preset load on a reference metallic sample having a known hardness and detecting the contact resistance under said load;
   functionally setting the tester on a metallic sample to be tested and gradually loading the indenter until the same electrical contact resistance as detected on said reference sample is measured by said electrical resistance measuring apparatus and reading the load which is actually applied to the indenter;
   determining the hardness of the tested sample through a proportionality relationship between said preset load applied to the reference sample and the load applied to the tested sample for attaining the same electrical contact resistance on the reference sample and on the test sample.

2. The method as defined in claim 1, wherein the testing is conducted with the surface of the sample being indented wetted with an oil.

3. The method as defined in claim 1 wherein said indenting tip has an electrical conductivity which is not greater than 1/10 of the electrical conductivity of said reference metal sample and/or of said metal sample to be tested.

4. The method as defined in claim 1, further comprising
   repeatedly recording paired values of applied load and corresponding electrical contact resistance during the loading up of the indenter to a preset load on said reference sample;
   repeatedly recording paired values of applied load and corresponding electrical contact resistance while gradually loading the indenter on the metallic sample to be tested;
   determining the hardness of the tested sample through a proportionality relationship between loads corresponding to identical electrical contact resistances detected on the reference sample and on the tested sample, for a certain interval of the applied load.

* * * * *